United States Patent
Voth et al.

(10) Patent No.: US 11,931,095 B1
(45) Date of Patent: Mar. 19, 2024

(54) METHOD AND SYSTEM FOR DETERMINING BASELINE ELECTRODE IMPEDANCE FOR TISSUE CONTACT DETECTION

(71) Applicant: St. Jude Medical, Cardiology Division, Inc., St. Paul, MN (US)

(72) Inventors: Eric J. Voth, Maplewood, MN (US); Jeffrey A. Schweitzer, St. Paul, MN (US); Linda L. Ruetz, New Brighton, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 18/096,214

(22) Filed: Jan. 12, 2023

(51) Int. Cl.
  *A61B 5/053* (2021.01)
  *A61B 18/12* (2006.01)
  *A61B 18/00* (2006.01)

(52) U.S. Cl.
  CPC .......... *A61B 18/1206* (2013.01); *A61B 5/053* (2013.01); *A61B 2018/00875* (2013.01)

(58) Field of Classification Search
  CPC ..... A61B 5/053; A61B 5/0538; A61B 5/6852; A61B 5/7221; A61B 5/7225; A61B 18/1206; A61B 18/1492; A61B 2018/00875; A61B 2090/065
  See application file for complete search history.

(56) References Cited

U.S. PATENT DOCUMENTS

| | | | |
|---|---|---|---|
| 10,188,314 B2 | 1/2019 | Mosesov et al. | |
| 10,398,348 B2 * | 9/2019 | Osadchy | A61B 5/6886 |
| 10,750,974 B2 | 8/2020 | Curran | |
| 10,799,148 B2 | 10/2020 | Mosesov et al. | |
| 11,179,194 B2 | 11/2021 | Sliwa et al. | |
| 11,439,319 B2 | 9/2022 | Curran | |
| 11,612,334 B2 | 3/2023 | Mosesov et al. | |
| 11,612,335 B2 | 3/2023 | Mosesov et al. | |
| 2017/0348049 A1 | 12/2017 | Vrba et al. | |
| 2019/0183378 A1 * | 6/2019 | Mosesov | A61B 5/068 |
| 2022/0192604 A1 * | 6/2022 | Palti | A61B 5/283 |
| 2023/0077196 A1 | 3/2023 | Curran | |

* cited by examiner

*Primary Examiner* — Devin B Henson
(74) *Attorney, Agent, or Firm* — Billion & Armitage

(57) ABSTRACT

A method of determining a baseline impedance value for a first electrode in a plurality of electrodes located on a medical device for tissue contact detection includes measuring an impedance value of the first electrode generated in response to a drive signal to the first electrode. The method further includes assigning a baseline impedance value to the first electrode based on impedance values measured in a predetermined time interval and determining a confidence value associated with the baseline impedance value. The method further includes utilizing the baseline impedance value in determining contact status of the first electrode when the confidence value is at or above a predetermined threshold value.

14 Claims, 8 Drawing Sheets

METHOD AND SYSTEM FOR DETERMINING BASELINE ELECTRODE IMPEDANCE FOR TISSUE CONTACT DETECTION

TECHNICAL FIELD

The present invention relates generally to catheters and methods and systems of detecting tissue contact based on electrode impedances.

BACKGROUND

Catheters are utilized in a number of operations within the human body. In many of these applications, whether collecting data from surrounding tissue or administering treatment, it is important to determine the proximity of the catheter—in particular the electrodes collecting data or administering treatment—with the adjacent tissue. A number of methods are utilized to make this determination, including for example monitoring electrocardiogram signals (e.g., voltage measured between electrodes) and/or impedance of an electrode. For example, impedance is understood, in general, to increase in response to contact with tissue. However, a number of other factors may also result in variations in impedance, including location of the electrode within the body (i.e., different chambers of the heart, exposed to different volumes of blood flow, may exhibit different impedance values) and movement of the surrounding tissue as a result of, for example, heartbeats.

To evaluate whether an electrode is in contact with tissue, a measured impedance can be compared to a baseline value that represents the impedance magnitude when, by definition, that electrode is not near tissue. However, the baseline value is highly variable including from patient to patient and procedure to procedure and needs to be determined for each electrode at least once during a procedure. Moreover, it can be difficult to establish times when a given electrode has been moved away from tissue. It would be beneficial to develop a method and system for assessing the quality of a particular baseline value for each electrode on a catheter.

SUMMARY

According to one aspect, a method of determining a baseline impedance value for a first electrode in a plurality of electrodes located on a medical device for tissue contact detection includes measuring an impedance value of the first electrode generated in response to a drive signal to the first electrode. The method further includes assigning a baseline impedance value to the first electrode based on impedance values measured in a predetermined time interval and determining a confidence value associated with the baseline impedance value. The method further includes utilizing the baseline impedance value in determining contact status of the first electrode when the confidence value is at or above a predetermined threshold value.

According to another aspect, a method of assessing confidence in a baseline impedance value for a first electrode in a plurality of electrodes includes applying drive signals between the first electrode and a second electrode in the plurality of electrodes, the first and second electrodes forming a pair. A bipolar electrode complex impedance (BECI) value is measured for the first electrode generated in response to the drive signal and a baseline BECI value is determined for the first electrode, the baseline BECI value being a first minimum BECI value measured during a first predetermined time interval that is greater than a predetermined lower threshold and less than a predetermined upper limit. The method further includes determining tissue contact based on the measured BECI value being greater than the baseline BECI value by a predetermined amount during a second time interval and assigning a confidence state for the baseline BECI value based, at least in part, on measured BECI values for the first electrode.

A method of determining a baseline impedance value for a first electrode in a plurality of electrodes located on a medical device for tissue contact detection includes measuring an impedance value of the first electrode generated in response to a drive signal to the first electrode and measuring an impedance value for each of the other electrodes in the plurality of electrodes, the impedance value generated in response to a drive signal to each of the other electrodes. A baseline impedance value is assigned to the first electrode based on a minimum impedance value measured in a predetermined time interval and a confidence value associated with the baseline impedance value is determined based on measured BECI values for the first electrode and measured BECI values for one or more of the other electrodes in the plurality of electrodes. The baseline impedance value is utilized to determine contact status of the first electrode when the confidence value is at or above a predetermined threshold value.

DETAILED DESCRIPTION

According to some embodiments, the claimed invention facilitates quantifying the quality of the baseline impedance value for each electrode among a plurality of electrodes on a medical device. The baseline impedance is defined as the impedance magnitude when the electrode is not near tissue.

The baseline impedance value may be utilized in tissue contact algorithms for determining tissue contact status of an electrode, and thus, a quality baseline value for impedance is central to accurately determining tissue contact status. If the baseline impedance is set too low, the electrode may be extra sensitive to tissue proximity and results may indicate false contact. If the baseline impedance is set too high, the electrode may be unlikely to ever indicate firm contact with tissue. The method disclosed herein allows for the baseline impedance to be reset where appropriate. The method includes repeated baseline measurements intermixed with intervals that specifically include evidence of tissue contact.

Quantifying the quality of the baseline impedance value for an electrode can include incrementally increasing a confidence state of that electrode based on impedance data collected for that electrode. In some embodiments, the confidence state is further increased based on impedance data collected for other electrodes on the medical device. The plurality of electrodes on the medical device can be arranged in pairs. Each electrode can have its own baseline impedance value and each pair can have a "paired baseline" (pairedBL) value which is an average of the baseline impedance value of each of the two electrodes in the pair. The objective is to obtain, for each electrode, the lowest stable impedance value for use as the baseline impedance value, and as more data is collected, to have increasing confidence in the quality of that baseline value. The confidence state or confidence level can be used in determining whether to use the baseline impedance in determining tissue contact status.

Figure 1:
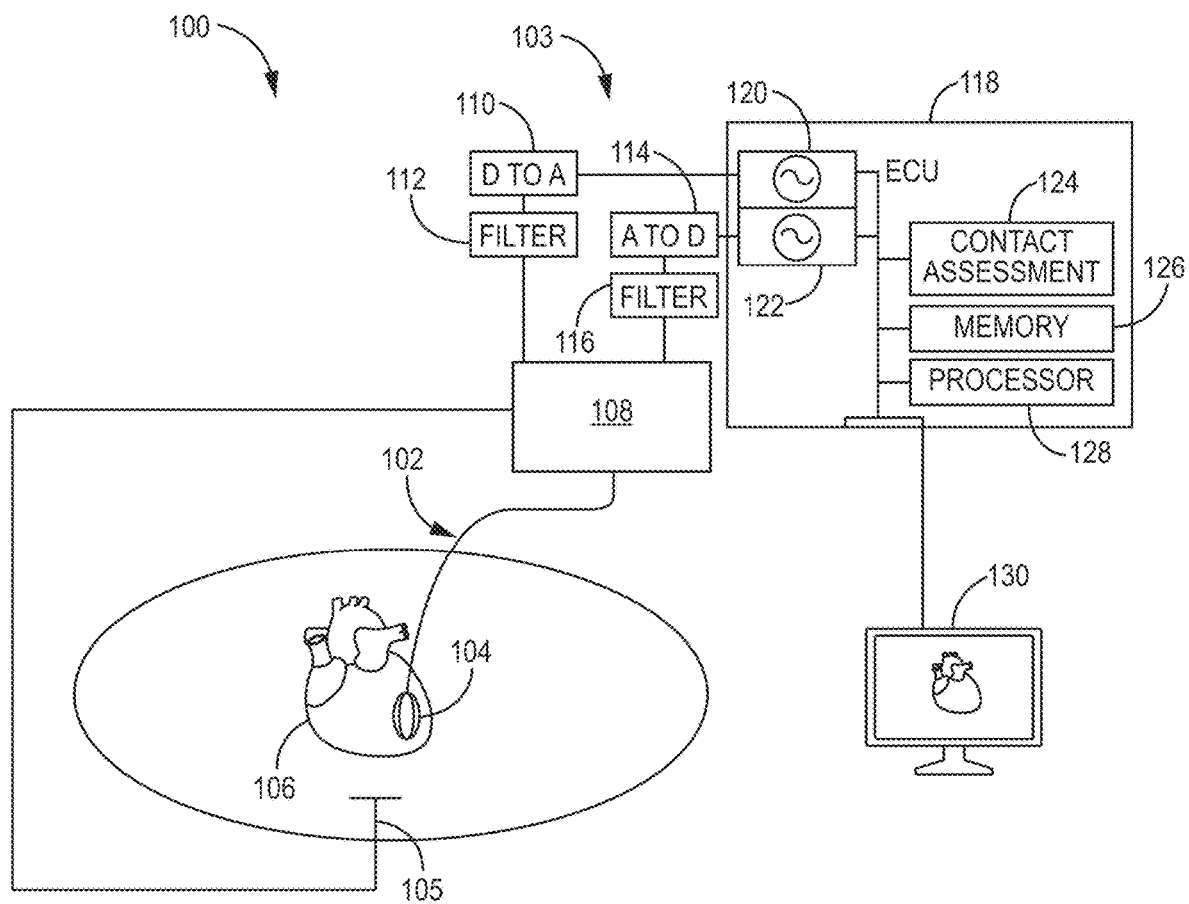
FIG. 1 is a diagrammatic depiction of a system including a medical device for insertion within a patient, the system configured to utilize impedances between electrodes to determine contact status of the one or more electrodes located at a distal end of the medical device according to some embodiments.

FIG. 1 is a diagrammatic depiction of a system 100 including a medical device 102 and a local system 103. In some embodiments, the local system includes a switch 108, a digital-to-analog (D to A) converter 110, a filter 112, an analog-to-digital (A to D) converter 114, a filter 116, a display 130, and an electronic control unit (ECU) 118 that may include a signal source 120, a synchronous demodulator circuit 122, a contact assessment module 124, a memory 126, and a processor 128. In some embodiments, one or more surface patch electrodes 105 may be adhered to the skin of the patient.

In some embodiments, the medical device 102 is an elongate medical device, such as a diagnostic and/or therapy catheter, an introducer, sheath, or other similar type of device. The medical device 102 includes a distal end 104 and a proximal end (not shown) that includes a handle operated by a technician as well as interfaces for interfacing the medical device 102 to the local system 103. The distal end 104 may include various sensors and/or components for localization/navigation of the distal end 104 within the patient, mapping of physiological parameters within the patient, and delivery of therapy. In particular, the distal end 104 of the medical device includes a plurality of electrodes that may be utilized for one or more of these purposes.

In some embodiments, contact status of the one or more electrodes located at the distal end 104 of the medical device 102 is determined based on one or more electrical characteristics measured at the electrode. For example, in some embodiments the measured electrical characteristic is a bipolar electrode complex impedance (BECI) generated by driving an excitation signal between two electrodes forming a bipolar pair. The resulting voltage at each of the electrodes is measured and utilized to derive a complex impedance signal. In some embodiments, contact assessment module 124 utilizes the BECI measurements, either alone or in combination with other measured electrical characteristics, to determine the contact status of each electrode. In some embodiments, the term "contact status" is a binary determination, with the electrode either being "in contact" with the tissue or "not in contact" with the tissue. In other embodiments, the term "contact status" may include additional contact states, such as "intermittent contact". In still other embodiments, the term "contact status" may describe a proximity of the electrode to adjacent tissue.

In the embodiment shown in FIG. 1, signal source 120 is utilized to generate the excitation signal. In some embodiments, signal source 120 generates one or more excitation or drive signals, each at a unique frequency. More specifically, the signal generator 120 may generate a plurality of excitation or drive signals having unique frequencies within a range from about 1 kHz to over 500 kHz, more typically within a range of about 2 kHz to 200 kHz, and even more typically between about 10 kHz and about 20 kHz, in one embodiment. The drive signals may each have a constant current, typically in the range of between 1-200 µA, and more typically about 5 µA, in one embodiment. The signal generator 120 may also generate signals involved in, for example, determining a location of the electrodes within the body of the patient that may be utilized for mapping, navigation, and/or therapy delivery. The digital signal(s) generated by the signal source 120 are converted to analog signal(s) by D-to-A converter 110 and provided via filter 112 and switch 108 to selected bipolar electrodes. In response to the analog signals supplied between selected bipolar electrodes, a resulting voltage is measured at the electrode pairs by the switch 108, the filter 116, the A-to-D converter 114, and a synchronous demodulator circuit 122. In some embodiments, switch 108 selects the electrode to monitor in response to the excitation or drive signal delivered. The filter 116 and the A-to-D converter 114 convert the analog signal to a digital signal that can be operated on by the ECU 118, The synchronous demodulator circuit 122 isolates signals from one another based on the frequency of the excitation or drive signal, allowing a plurality of bipolar electrode pairs to be analyzed approximately simultaneously based on the plurality of excitation or drive signals supplied to the electrode pairs.

In some embodiments, the memory 126 may be configured to store data respective of the medical device 102, the patient, and/or other data (e.g., calibration data). Such data may be known before a medical procedure (medical device specific data, number of catheter electrodes, etc.), or may be determined and stored during a procedure. The memory 126 may also be configured to store instructions that, when executed by the processor 128 and/or a contact assessment module 124, cause the ECU 118 to perform one or more methods, steps, functions, or algorithms described herein. For example, but without limitation, the memory 126 may include data and instructions for determining impedances respective of one or more electrodes on the medical device 102 and utilizing the impedance measurements to determine a contact status of the one or more electrodes. In addition, the memory 126 may include data and instructions for determining and quantifying quality of a baseline impedance value. In some embodiments, the contact assessment module 124 utilizes a processor executing instructions stored on the memory 126, an application specific integrated circuit (ASIC), or other type of processor. The ECU may be connected to a display 130, which may display an output of sensed tissue (e.g., heart), the medical device (not shown) and/or determined contact status of the one or more electrodes of the medical device 102.

Figure 2:
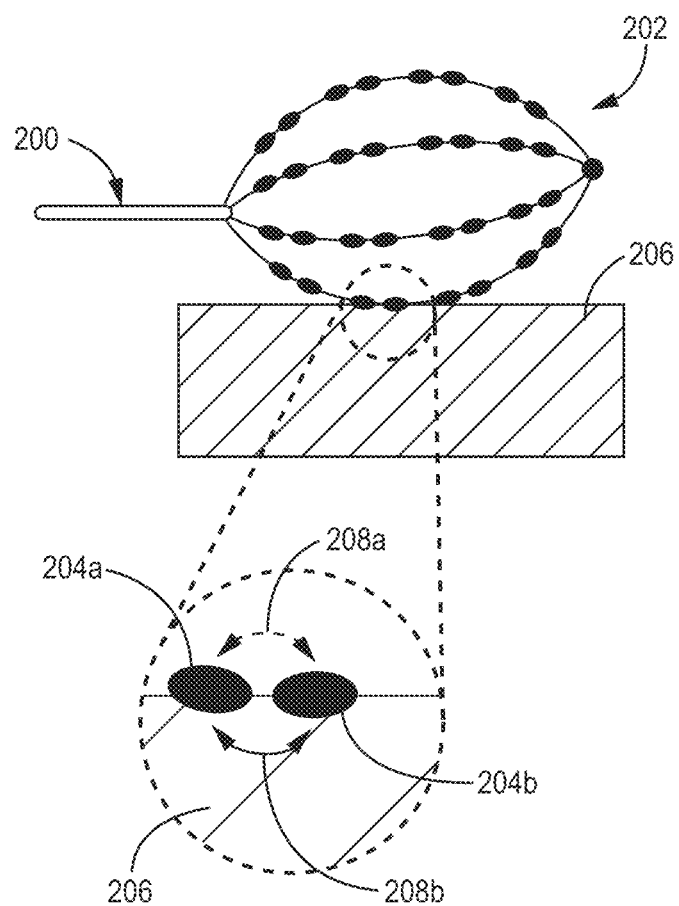
FIG. 2 is a diagrammatic depiction of a distal end of a medical device having a plurality of splines and a plurality of electrodes located on each spline positioned adjacent to cardiac tissue according to some embodiments.

FIG. 2 is a diagrammatic depiction of a distal end 104 of a medical device 102 having a plurality of splines and a plurality of electrodes 204a, 204b located on each spline positioned adjacent cardiac tissue according to some embodiments. In the embodiment shown in FIG. 2, electrodes 204a and 204b form a bipolar electrode pair. In some embodiments, an impedance measurement is generated by supplying an excitation signal to electrodes 204a and 204b, resulting in current flowing between the electrodes 204a and 204b as shown by dashed arrows 208a, 208b. The passage of at least a portion of the current 208a, 208b through the patient tissue 206 at the electrode-tissue interface affects the inductive, capacitive, and/or resistive effects of the electrode response to the drive signal(s). That is, the tissue contact affects the impedance measurements of the electrodes 204a, 204b. In general, if the electrodes 204a, 204b are not in contact with the tissue 206, then the circuit is formed within the blood pool of the patient and the impedance measurement decreases due to the conductive path formed within the blood pool. If the circuit path includes tissue 206 as shown in FIG. 2, then the impedance measurement increases, reflecting the higher impedance of the tissue 206 as compared with measurements taken within the blood pool. Impedance measurements are utilized to determine tissue contact status of the electrodes. In some embodiments, contact status may include a determination of in contact or not in contact. In other embodiments, contact status may include other contact status, such as intermittent contact, or a range of contact states. In some embodiments, the impedance measured is a bipolar, complex impedance (BECI) value.

In other embodiments, the distal end 104 of the medical device 102 may incorporate a plurality of different geometries and/or designs. The embodiment shown in FIG. 2 includes a plurality of splines positioned in a basket geometry, wherein each spline includes a plurality of electrodes. The embodiment shown in FIG. 4 similarly includes a plurality of splines, each spline including only a single electrode. In other embodiments, the distal end of the medical device 202 is a grid-like array of electrodes shown in more detail in FIG. 3. In other embodiments, the distal end of the medical device may be curved or loop-like, with a plurality of electrodes spaced along the distal end. Likewise, a variety of different types, geometries, and sizes of electrodes may be utilized at the distal end of the medical device.

Figure 3:
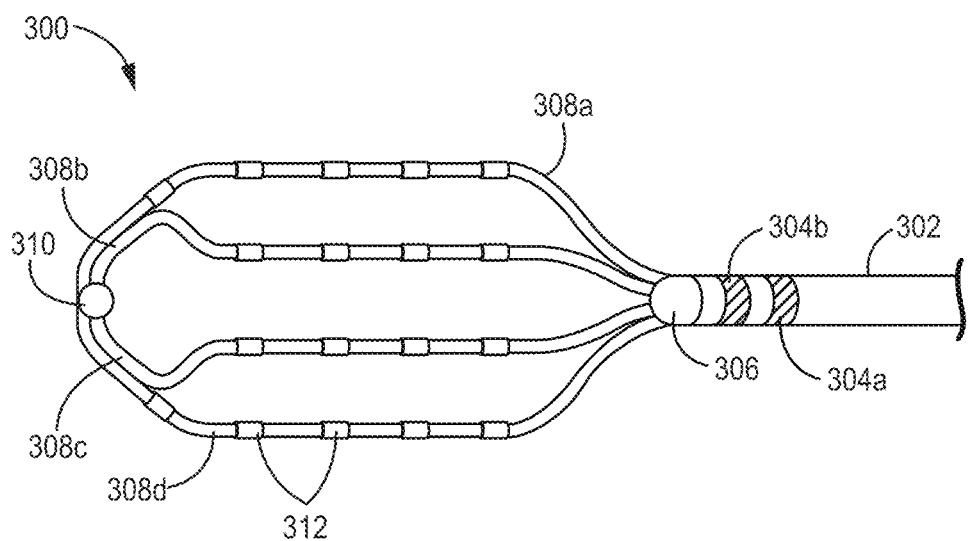
FIG. 3 is a diagrammatic depiction of a distal end of a medical device having a plurality of splines, each spline including a plurality of electrodes organized in a grid-like array according to some embodiments.

FIG. 3 is top view of a grid array catheter 300. In some embodiments, grid array catheter 300 includes a shaft 302, shaft electrodes 304a and 304b, a proximal end 306, a plurality of splines 308a, 308b, 308c, 308d, a distal end 310, and a plurality of spline electrodes 312. In some embodiments, bipolar electrode complex impedance measurements may be taken between any pair of adjacent electrodes. For example, an impedance measurement may be taken between shaft electrodes 304a, 304b. In other embodiments, an impedance measurement may be taken between any pair of spline electrodes 312. As described above, in some embodiments the impedance measurement is a BECI measurement.

Figure 4:
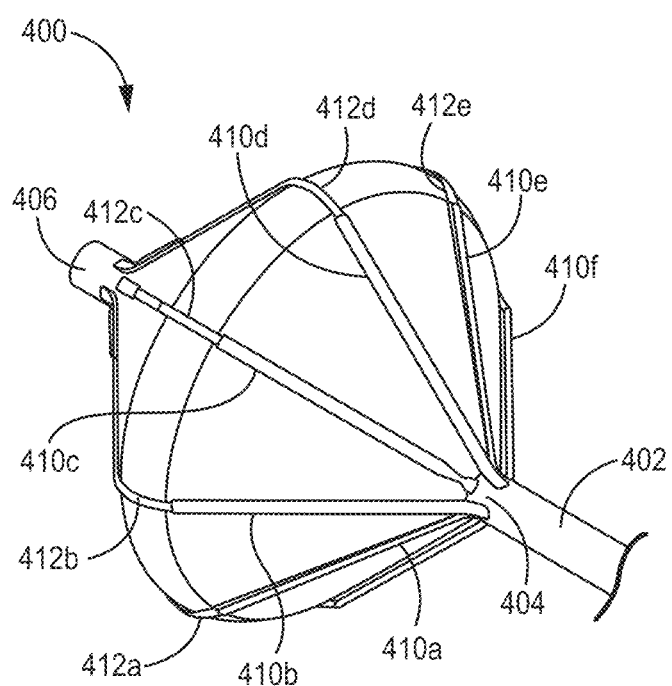
FIG. 4 is a diagrammatic depiction of a distal end of a medical device having a plurality of splines, each spline including a plurality of electrodes organized in a basket-like array according to some embodiments.

FIG. 4 is an isometric view of a basket catheter 400. In some embodiments, basket catheter 400 includes a shaft 402, a proximal end 404, a distal end 406, and a plurality of splines 410a-410f extending between the proximal end 404 and the distal end 406. Each of the plurality of splines 410a-410f includes a corresponding electrode 412a-412f. In some embodiments, BECI measurements may be taken between pairs of adjacent electrodes such as between electrode 412a and 412b, or between electrodes 412c and 412d.

Figure 5:
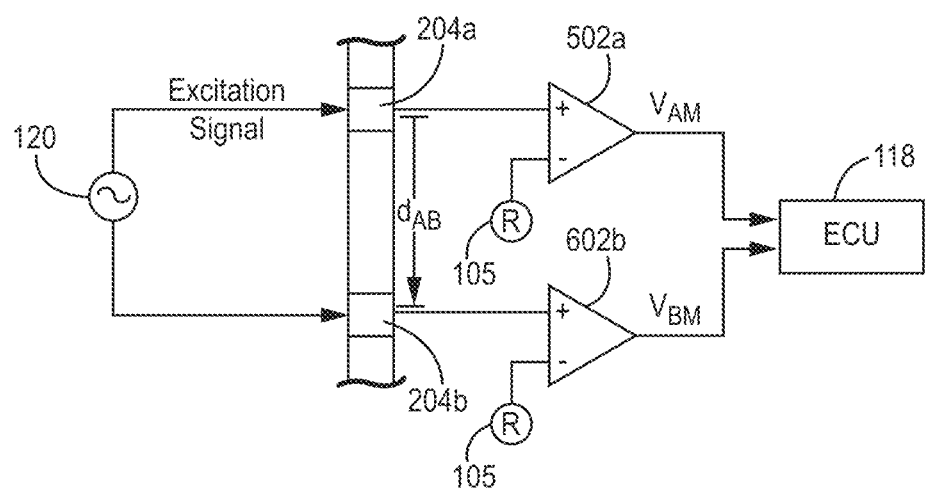
FIG. 5 is a diagrammatic view of components utilized to measure impedance between two electrodes located on the medical device according to some embodiments.

FIG. 5 is a circuit diagram illustrating the circuit elements utilized to excite the bipolar pair of electrodes and measure the resulting complex impedance according to some embodiments. In particular, the circuit diagram includes a signal source 120 (also shown in FIG. 1), a pair of electrodes 204a, 204b (shown in FIG. 2), first and second operational amplifiers 502a, 502b, and ECU 118 (also shown in FIG. 1). In some embodiments, the signal source 120 generates an excitation signal that is provided to first and second electrodes 204a, 204b. The first op-amp 502a includes a first terminal (e.g., positive terminal) connected to the first electrode 204a and a second terminal (e.g., negative terminal) connected to a reference electrode 105 (e.g., surface electrode). The output of the op-amp 502a reflects the difference in voltage between the first electrode 204a and the reference electrode 105. The second op-amp 502b includes a first terminal (e.g., positive terminal) connected to the second electrode 204b and a second terminal (e.g., negative terminal) connected to a reference electrode 105 (e.g., surface electrode). The output of the op-amp 502b reflects the difference in voltage between the second electrode 204b and the reference electrode 105. The respective outputs of the first op-amp 502a and the second op-amp 502b are provided to the ECU 118, which utilizes the respective measurements to determine the bipolar electrode complex impedance (BECI).

Figure 6:
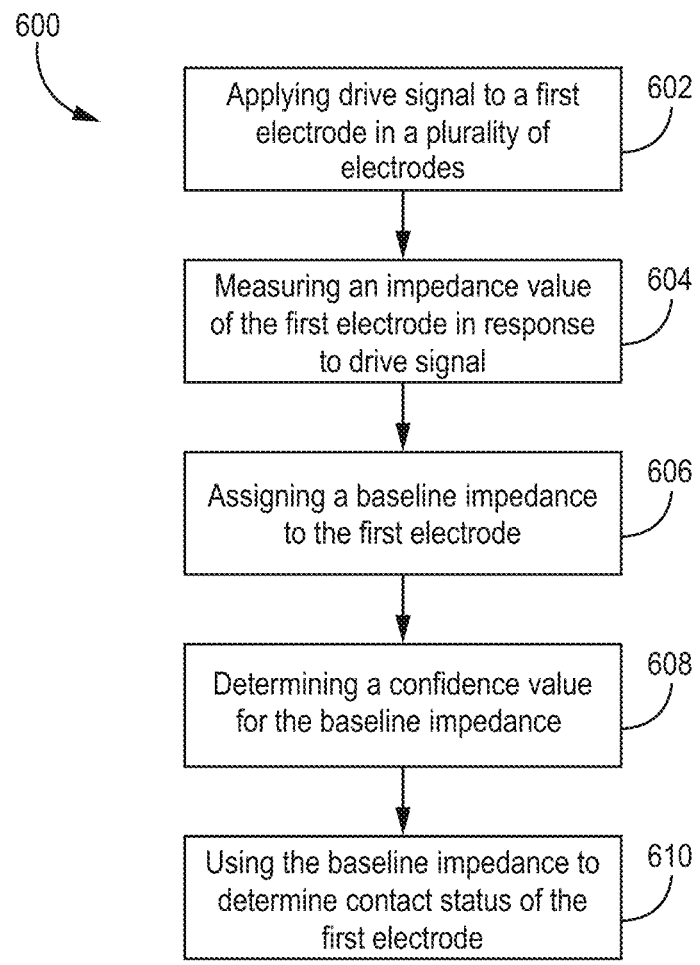
FIG. 6 is a flowchart illustrating steps utilized to determine a baseline impedance value for a first electrode in a plurality of electrodes according to some embodiments.

FIG. 6 is a flowchart illustrating steps in a method 600 utilized to determine a baseline impedance value for a first electrode among a plurality of electrodes as well as a confidence level associated with the baseline impedance according to some embodiments. In some embodiments, the algorithm is applied to each of the plurality of electrodes separately. However, as described in more detail below, in some embodiments, the determination of confidence level associated with a determined baseline impedance is based, in part, on the baseline impedance and/or determined confidence of other of the plurality of electrodes. The plurality of electrodes can be arranged on a catheter, such as, for example, either of the catheters shown in FIGS. 2, 3 and 4. At step 602, a drive signal is applied to the first electrode as described above. More specifically, the drive signal can be applied between the first electrode and a second electrode, the first and second electrodes forming a first pair. At step 604, an impedance value of the first electrode is measured over a time interval in response to the drive signal. According to some embodiments, the measured impedance is a bipolar electrode complex impedance (BECI). The impedance measurements can be collected as the catheter is actively moved around the cardiac chamber to gather impedance measurements when the electrode is in the blood pool as well as when the electrode is in contact with tissue.

At step 606, a baseline impedance is assigned to the first electrode. In some embodiments, the baseline impedance is the minimum impedance detected or measured over the time interval. In some embodiments, the baseline impedance is not merely the minimum impedance detected within the time interval. For example, in some embodiments, the baseline impedance is determined as an average of selected minimum impedances measured within the time interval (e.g., 10 lowest measured impedances selected from the time interval and averaged). In some embodiments, the baseline impedance may be selected based on a percentile of the measured impedances (e.g., the impedance located at the tenth percentile of monitored impedances is selected as the baseline impedance). In some embodiments, selecting the baseline value—even initially—as something other than a minimum value removes clearly erroneous impedance values from being selected as representative of the baseline. This may include situations in which the electrodes come into contact with one another and present an extremely low impedance value not representative of a baseline (e.g., in the blood pool) value. In some embodiments, rather than utilize an average or percentile, one or more constraints are included at step 606 to ensure that the detected minimum impedance is a reasonable indication that the electrode is not near tissue (i.e. in the blood pool) and is therefore a good candidate for a baseline value. For example, such constraints can include: the range of measured impedances (i.e., maximum impedance value less the minimum impedance value) is less than a first predetermined value (i.e. low variability), the minimum value is greater than a second predetermined value (i.e., the baseline value selected must be greater than this predetermined value), and/or the minimum value is less than a third predetermined value (i.e., the baseline value cannot be greater than a predetermined value). In some embodiments, these constraints ensure that the baseline value is reasonable. It is recognized that other parameters or constraints can be used to provide assurance that the minimum impedance value is likely taken in the blood pool. If the constraints are met, the measured minimum impedance can be used as the baseline impedance for the first electrode. If these constraints are not met, then additional measurements can be taken for the first electrode until the measured minimum impedance can be assigned to the first electrode.

Figure 7:
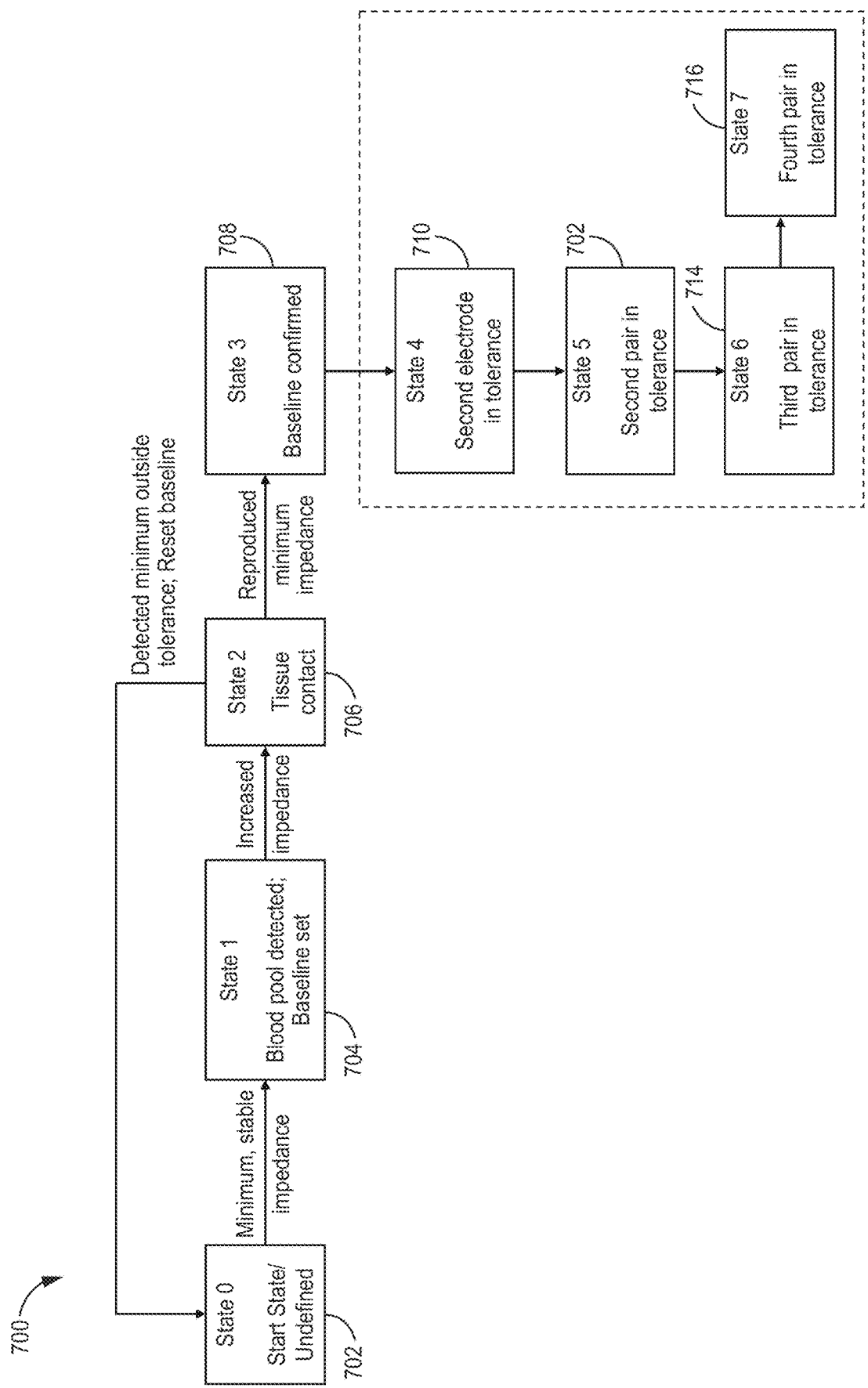
FIG. 7 illustrates a state machine for determining a confidence state associated with a baseline impedance value for the first electrode according to some embodiments.

At step 608, a confidence value can be determined for the assigned baseline impedance. Initially, the confidence value is low (e.g., state 0). The confidence value increases as impedance data is collected for the first electrode which confirms that the impedance value selected is appropriate. In some embodiments, the confidence value is also based on the impedances and confidence values associated with additional electrodes among the plurality of electrodes. In some embodiments, the confidence value is incremented (and possibly decremented) according to a state machine model, for example as shown in FIG. 7 and described below. Transition from one state to the next is conditioned on satisfaction of one or more conditions, wherein each state represents a quantified confidence level (i.e., each state indicates a quantified confidence associated with the selected baseline value). Just as the confidence value can increase under step 608 as additional data is collected, the confidence value can also decrease and the method 600 can include resetting the baseline impedance under certain conditions.

According to some embodiments, the confidence state or confidence level can be displayed to a technician via a display. The display can include numerical values of the confidence state and/or level associated with each electrode. Alternatively, or in addition to numerical values, the display can use color coding or other graphical elements, such as a graphical representation of each electrode and associated confidence level (e.g., color coded to indicate quickly to a user the confidence value associated with determined contact status), to visually represent whether a confidence level threshold is met for each electrode on the medical device.

At step 610, the contact status of the first electrode is determined based on the baseline impedance value and a current (i.e., most recent) impedance value. A quality baseline impedance is needed for optimum results of the algorithm used for contact status with tissue. The tissue contact algorithm compares a measured impedance value relative to the baseline impedance value. If the assigned baseline impedance is too low, the first electrode is overly sensitive to tissue proximity and the algorithm may indicate a false positive for tissue contact. On the other hand, if the assigned baseline impedance is too high, confirmation of tissue contact may likely never happen. As such, a quality baseline impedance is crucial to effectively determining contact status. In some embodiments, the confidence value assigned at step 608 is utilized to determine whether a tissue contact status can be determined. For example, in some embodiments tissue contact is determined only if the confidence value associated with the baseline impedance is equal to or greater than a selected threshold. In other embodiments, the tissue contact status is determined regardless of the confidence value determined at step 608, but the confidence value is displayed along with the tissue contact status to provide an indication to the user of the confidence associated with the determined tissue contact status. If the confidence level in the assigned baseline impedance is too low, it may not be prudent to adopt the baseline impedance in the tissue contact algorithm.

According to some embodiments, the method 600 can include setting a confidence level threshold that must be met before the baseline impedance value can be utilized under step 610 in determining contact state. The confidence level threshold can be based on a percentage. In addition to or as an alternative to a percentage value, the confidence level threshold can correspond to a state number in the state machine.

FIG. 7 is a state machine diagram 700 indicating conditions and criteria utilized to quantify a confidence value for the first electrode according to some embodiments. Each state represents an increasing confidence (quantified confidence) associated with a determined baseline impedance value. In some embodiments, the baseline impedance selected remains unchanged, but the confidence value associated with the selected baseline impedance value increases as the electrode progresses through the state machine (i.e., progression from state 704 to state 706 would result in an increase in the confidence value associated with a determined baseline impedance).

Many variations of the state machine 700 are within the scope of the present invention including additional or alternative logic. The states are briefly described immediately below, and then additional detail follows for each state. The state machine 700 is described in reference to the first electrode, but it is recognized that the state machine can be used for each electrode among the plurality of electrodes on the medical device. Zero state 702 is a start state or "undefined". (Each electrode starts at state 702.) Zero state 702 represents a zero-confidence or initial state. The electrode progresses from zero state 702 to first state 704 in response to a first condition being satisfied. For example, in one embodiment, the first condition is detection of a "low and quiet" interval of measured impedance magnitude indicative of the electrode being located in the blood pool. At first state 704, a baseline impedance value is selected, but the confidence value associated with baseline impedance is set to a value indicative of state 704 (i.e., relatively low). The first electrode progresses from the first state 704 to the second state 706 in response to a detected increase or sufficiently high impedance value indicative of tissue contact. The detection of increased impedance—relative to the baseline impedance set at the first state 704—increases confidence in the baseline impedance value because it confirms that the baseline impedance is likely a baseline or low impedance value. The first electrode progresses from the second state 706 to the third state 708 when there is another low and quiet interval in which the baseline impedance is confirmed. At the third state 708, confirmation of the baseline impedance (set at the first state 704) further increases the confidence value associated with the baseline impedance value.

In some embodiments, a number of additional states may be utilized to further increase the confidence value associated with the baseline impedance value. In some embodiments, the electrode progresses from the third state 708 to a fourth state 710 in response to its paired electrode (the second electrode) also progressing to state 708. That is, if the confidence value of each electrode in an electrode pair reaches a threshold value (e.g., third state 708), then the confidence value associated with both electrodes increases further from the third state 708 to the fourth state 710. In some embodiments, the first electrode may be paired with more than one electrode and the confidence value of the baseline impedance associated with the first electrode may continue to increase (from the fourth state 710 to the fifth state 712, sixth state 714, and seventh state 716) based on a comparison with each additional pair of electrodes on the medical device. In the example shown in FIG. 7, the medical device or catheter has eight electrodes. Since there are three additional pairs of electrodes (in addition to the first pair defined as the first and second electrodes), there are states five, six and seven at 712, 714 and 716, respectively. Higher states correspond to greater confidence that the first electrode has detected a reasonable baseline value. In some embodiments, each state provides a quantified confidence value. For example, in an embodiment having eight states, each state may be assigned a confidence value with the zero state being assigned a '0' value and the seventh state being assigned a value of '1'. The intervening states are assigned decimal values increasing linearly from '0' to '1', but other embodiments are within the scope of the invention.

In some embodiments, the state machine 700 defines the operation of a baseline impedance algorithm that can be separate from the tissue contact algorithm described above for determining tissue contact. In some embodiments, the baseline impedance algorithm can be used for each electrode and can keep track of its state (which corresponds to the quantified confidence value), its current baseline value, a "candidate" baseline value (described below) and a moving window W of its impedance magnitude, of length WM samples (nominally 0.5 second, and all such future values are also nominal and not constraining). The moving window W is defined by a length of time and by predetermined minimum and maximum values for impedance magnitude. If at any time an impedance signal is deemed saturated or otherwise "invalid", the variables under the algorithm can be reset to their default values (window empty, state zero and ohm values set high).

For clarity, the first electrode is again used for the description, but it is recognized that each electrode begins in the zero state 702. In some embodiments, the baseline impedance algorithm moves the first electrode from the zero state 702 to the first state 704 when one or more of the following conditions of low variability are met: the window W for the first electrode has the full WM samples; its range (maximum impedance magnitude minus minimum impedance magnitude of the samples) is less than a first predetermined value (nominally 12 ohms); its minimum is greater than a second predetermined value (a minimum ohms value, such as, for example, 40 ohms), and less than a third predetermined value (a maximum ohms value, such as, for example, 86 ohms); its minimum is less than the current baseline (if a current baseline exists), and its state is is less than or equal to 1. In some embodiments, if these conditions are met, the criteria for "blood pool detected" are satisfied, indicating that at least some of the impedance measurements collected during the window correspond to impedance measurements made while the electrode is in the blood pool (i.e., corresponding with the desired baseline impedance). Thus, the baseline impedance value can be set based on one or more of the impedance values collected, and the electrode moves to the first state 704. In some embodiments, the selected baseline value is selected as a minimum impedance value measured during the window (that satisfies the criteria) while in other embodiments the selected baseline value may represent an average or percentile selected from the measured impedance values. In other embodiments, one or more of the criteria utilized above may be utilized alone or in combination with one another to transition from the zero state 702 to the first state 704. As described above, the transition from the zero state 702 to the first state 704 increases the confidence value associated with the baseline value.

In some embodiments, at the first state 704, the baseline impedance algorithm clears the window W, sets the impedance baseline, and sets/updates a "paired baseline" or "pairedBL" of the first pair (the first electrode and the second electrode) to be the average of the current baseline for the first electrode and the current baseline for the second electrode. As described in more detail below, the "paired baseline" is utilized to transition to higher states (i.e., greater confidence values) as a result of the baseline impedances for the electrode pairs being in agreement. In some embodiments, the window W is cleared and new impedance values are collected to determine whether to transition from the first state 704 to the second state 706. However, in other embodiments the window W continues moving with the collection of new impedance values and no clearing of the window W is required.

In some embodiments, the first electrode transitions from the first state 704 to the second state 706 when an impedance of increased magnitude is observed, which is indicative of tissue contact of the first electrode. Specifically, if the measured impedance exceeds the current baseline impedance by more than a fourth predetermined value (for example, 10 ohms, or alternatively a predefined percentage or factor), the algorithm determines that the electrode has come into contact with tissue. The detection of a higher impedance value indicative of tissue contact increases the confidence that the baseline value set at the first state 704 represents an impedance value measured within the blood pool. In this way, transition to the second state 706 increases the confidence value associated with the baseline value set at the first state 704. The baseline value itself does not change in the transition from the first state 704 to the second state 706, only the confidence value associated with the transition from the first state 704 to the second state 706.

In some embodiments, the electrode transitions from the second state 706 to the third state 708 when the baseline impedance algorithm detects a measured impedance that is near the current baseline impedance, confirming movement away from tissue and a return to the blood pool. This confirmation indicates that the baseline impedance value set at the first state 704 is likely accurate and therefore further increases confidence in the baseline impedance value. In some embodiments, the first electrode transitions from the second state 706 to the third state 708 in response to the minimum impedance value detected within the window W being less than some predetermined factor of the current baseline impedance (i.e., within some threshold value of the current baseline value, indicating that the baseline impedance value is a good estimate of the electrode impedance when in the blood pool). For example, the factor can be equal to 1.0+a predetermined window tolerance ("Window-Tolerance"), such as, for example, 0.03. In some embodiments, additional constraints may be imposed similar to those provided at the first state 704 to determine if the detected minimum value within the window W is representative of a baseline impedance value. For example, in some embodiments, the one or more additional constraints include the range of impedances within the window W being less than the first predetermined value, the minimum impedance detected in the window W being greater than the second predetermined value, and the minimum impedance detected in the window W being less than the third predetermined value. In some embodiments, if the minimum impedance value detected within the window W is less than some predetermined factor of the current baseline impedance (and one or more of the additional constraints are satisfied) then the electrode transitions to the fourth state 710. The confidence value associated with the baseline impedance value set for the first electrode at the first state 704 increases, although the baseline impedance value itself remains unchanged. If those conditions are met, the current baseline impedance is confirmed and does not change.

However, if the minimum impedance detected within the window W at the second state 706 is NOT near the baseline impedance value, this indicates that the baseline impedance value set at the first state 704 may not be representative of the baseline impedance within the blood pool. In some embodiments, the electrode transitions from the second state 706 back to the zero state 702, indicating a lack of confidence in the baseline value initially set at the first state 704. In particular, if the minimum impedance value measured within the window W while in the second state 706 is more than a predetermined factor of the current baseline and/or the minimum impedance is outside the predetermined tolerance range of the current baseline, then the electrode transitions from the second state 706 to the zero state 702 and the process begins again to select a baseline impedance value and build confidence in the selected value.

In some embodiments, the third state 706 may represent the highest confidence state. In this embodiment, the first electrode reaches the third state 706 based entirely on impedance measurements received from the first electrode. In some embodiments, progression to additional states 710, 712, 714, and/or 716 may be dependent on the measured baseline values of one or more paired electrodes. In some embodiments, the first electrode moves to the fourth state 710 if its paired electrode (the second electrode) is also in the third state 708 (or a higher state). In some embodiments, the first electrode moves to the fourth state 710 if the first and second electrodes have impedance values that are close enough to one another. In this case, if the second electrode is also in the third state 708 and the first electrode moves to the fourth state 710, then the second electrode would also move to the fourth state 710. In some embodiments, when the first and second electrodes transition to the fourth state 710, a "paired baseline" (pairedBL) value is determined that can be used for quantifying the confidence state of other electrodes on the medical device. In some embodiments, the "paired baseline" value is an average of the baseline impedance associated with the first electrode and the second electrode. In other embodiments, the "paired baseline" value may be the minimum of the baseline impedances associated with the first electrode and the second electrode.

In some embodiments, transition of the first electrode to the fifth state 712, the sixth state 714 and the seventh state 716 is based on a comparison of the paired baseline value associated with the first and second electrode to other pairs of electrodes. For each additional pair of electrodes having a "paired BL" value that is within the predetermined tolerance range of the baseline impedance value of the first electrode pair, the electrode transitions to the next state and correspondingly the confidence value associated with the baseline impedance associated with the first electrode increases in value. For an exemplary catheter with eight electrodes, the maximum confidence state is seven since there are three other pairs of electrodes and the confidence state can be increased from 4 to 7 if all three other pairs satisfy the criteria above.

In some embodiments, the baseline impedance can be reset if a lower baseline value is detected; the specifics for resetting the baseline impedance depend on what state the first electrode is in when the lower baseline value is detected. For example, with respect to the second state 706, the baseline impedance could be reset (and the electrode reverted back to first state 704) if the minimum impedance value measured within the window W while in the second state 706 is more than a predetermined factor of the current baseline and/or the minimum impedance is outside the predetermined tolerance range of the current baseline. Likewise, in some embodiments if the first electrode has transitioned to the third state 708 or higher, and a lower baseline is detected relative to the current baseline (for example, less than a factor of 1.0−WindowTolerance), the baseline is not automatically reset to the new lower baseline. Rather, the new lower baseline can be kept as a candidate baseline ("candidateBL") until the conditions associated with the second state 706 condition are met again for the first electrode and another low variability window is detected to confirm the candidate baseline. The low variability window or tolerance range is defined as the minimum impedance being less than or equal to: (1.0+WindowTolerance) multiplied by the candidate baseline ("candidateBL"). Once these conditions are met, the candidate baseline becomes the new baseline impedance value.

For any of the electrodes among the eight electrodes on the exemplary catheter used in the state machine 700, if an electrode is in state 3 and its paired electrode (or mate) is in state 3 or higher, the algorithm sets its state to 4 and updates the pairedBL for that pair. The paired electrode can also be updated immediately. Next, the baseline impedance algorithm can look through each of the other three pairs of electrodes, and for each other pair in state 4 whose pairedBL is within a relative factor of the paired tolerance range ("PairedTolerance", nominally 0.36), the algorithm can incrementally increase its state value by one. (Note that it is possible to have some electrode pairs at the maximum state 7 while others are not.) By monitoring the paired BLs of other electrode pairs, electrodes can progress through states 5 and 6 to state 7 (the highest quality state).

The highest quality state depends on the total number of electrodes on the catheter. The state machine 700 in FIG. 7 is based on a catheter with eight electrodes. It is recognized that a catheter with more than eight electrodes would have a higher maximum state and a catheter with less than eight electrodes would have a lower maximum state. For impedance measurements, such as BECI measurements, that rely on pairs of electrodes, the total number of electrodes for the state machine is always an even number.

In some embodiments, each state within the state machine represents a confidence value associated with the baseline impedance set for a given electrode and can be expressed as a confidence percent in the range of 0 to 100. Zero percent confidence represents the beginning or undefined state (state zero) in which there is no confidence that the current baseline value is correct, as no data has yet been collected. By contrast, one hundred (100) percent confidence represents the highest quality state, with high confidence that the baseline impedance value is correct. The progression from zero to 100 percent can occur in discrete steps corresponding to the number of states in the state machine. Again, the number of states is based on the number of electrodes on the catheter or medical device. The number of non-zero states is equal to 3+(n/2), with n being the number of electrodes. Using the same eight-electrode catheter as the example, the number of states is equal to 3+(8/2) or seven. At confidence state 2, the confidence level is equal to 2 divided by 7, or 29 percent. At confidence state 3, the confidence level is equal to 3 divided by 7, or 43 percent. Table 1 below shows the corresponding state decimal value which can be converted to a percentage.

TABLE 1

Summary of Various states in State Machine for an eight-electrode catheter

| State Number | State decimal value | Description |
|---|---|---|
| 0 | 0 | Start state, or return state after bad data requires a reset |
| 1 | 0.14 | Detected blood pool. Can return to this level if lower level is detected from state 3 |
| 2 | 0.29 | Tissue contact has been detected (impedance has increased 10 Ohms from previous blood pool value) |
| 3 | 0.43 | Confirmed blood pool with minimum value within tolerance of previous blood pool value |
| 4 | 0.57 | Both electrode and its pair at State 3 |
| 5 | 0.71 | Average of electrode and its mate (pairedBL) match average of another pair within certain percentage |
| 6 | 0.86 | Average of electrode and its mate (pairedBL) match average of two pairs within certain percentage |
| 7 | 1 | Average of electrode and its mate (pairedBL) match average of all three other pairs within certain percentage |

The eight-electrode catheter is used as an example to illustrate how the state machine works. It is recognized that the state machine concept can be applied to any even number of electrodes. For a catheter with "n" electrodes, there can be "n" state machines that are simultaneously being executed. As another example, for a six-electrode catheter, the number of non-zero states is equal to 3+(6/2), or six total states. In yet another example, for a ten-electrode catheter, the number of non-zero states is equal to 3+(10/2), or eight total states.

Figure 8:
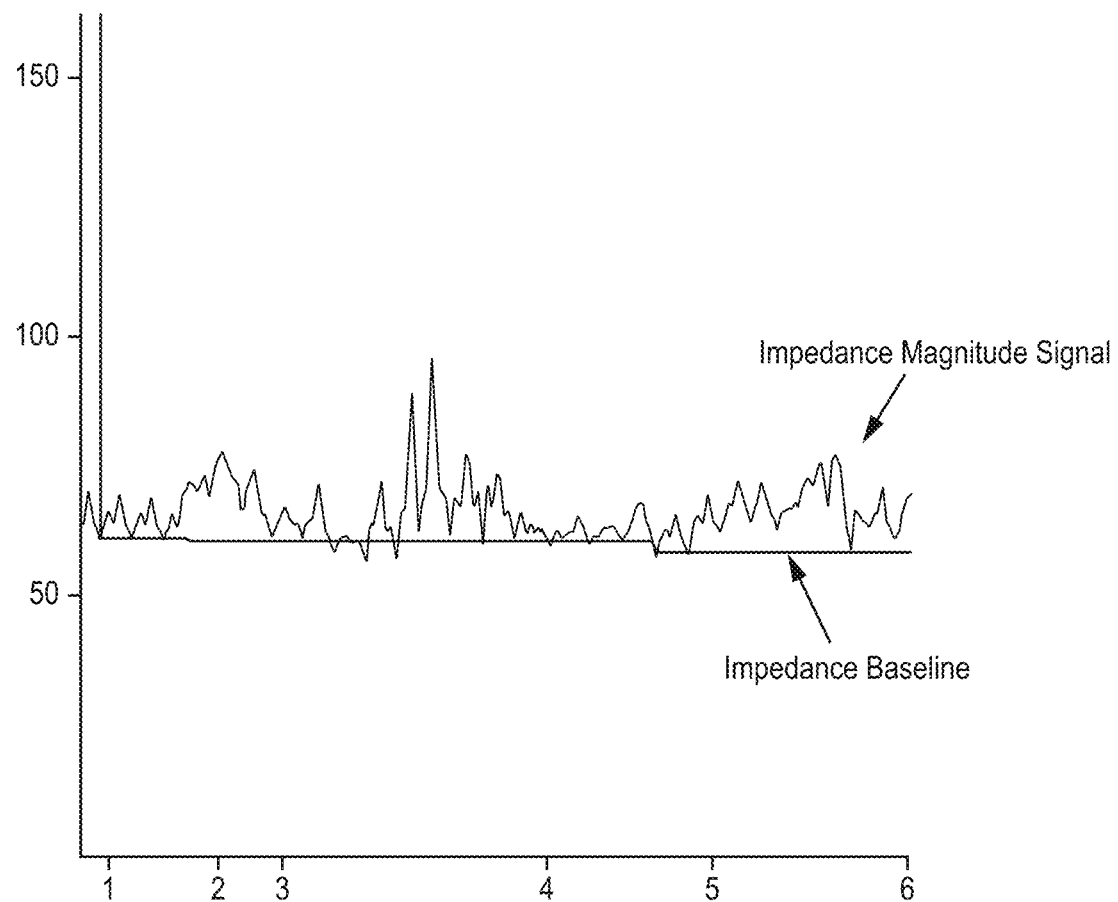
FIG. 8 is a plot illustrating an example impedance magnitude signal and the corresponding baseline impedance value and confidence state according to some embodiments.

FIG. 8 is a plot showing an example impedance magnitude signal for an electrode, as well as the baseline impedance as set by the baseline impedance algorithm described above. FIG. 8 also shows the time on the x-axis at which each confidence state is attained for the electrode.

As shown in FIG. 8, the baseline value is set at confidence state 1; there is an noticeable increase in impedance magnitude (about 10 ohms) at confidence state 2. At confidence state 3, the detected minimum impedance is about the same as the baseline impedance value, confirming repeat detection in the blood pool. A lower baseline is found between states 4 and 5. Because the confidence state was greater than 3 when the lower minimum impedance was detected, the confidence state can continue to increase rather than reverting back to states 0 and 1. However, the new lower minimum impedance is not immediately accepted (rather, the algorithm designates it as a candidate baseline) until there is another peak observed, indicating tissue contact.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

DISCUSSION OF POSSIBLE EMBODIMENTS

The following are non-exclusive descriptions of possible embodiments of the present invention.

According to some embodiments, a method of determining a baseline impedance value for a first electrode in a plurality of electrodes located on a medical device for tissue contact detection includes measuring an impedance value of the first electrode generated in response to a drive signal to the first electrode and assigning a baseline impedance value to the first electrode based on impedance values measured in a predetermined time interval. The method may further include determining a confidence value associated with the baseline impedance value and utilizing the baseline impedance value in determining contact status of the first electrode when the confidence value is at or above a predetermined threshold value.

The method of the preceding paragraph can optionally include, additionally and/or alternatively any, one or more of the following features, steps, configurations and/or additional components.

For example, the step of assigning a baseline impedance value to the first electrode may further include selecting a minimum impedance value measured in the predetermined time interval.

In some embodiments, the minimum impedance value becomes the assigned baseline impedance value if the minimum impedance value is greater than a predetermined impedance threshold and less than a predetermined impedance limit.

In some embodiments, the impedance value is a bipolar electrode complex impedance (BECI) value resulting from applying the drive signal between the first electrode and a second electrode in the plurality of electrodes.

In some embodiments, the step of determining a confidence value associated with the baseline impedance value may further include incrementally increasing the confidence value based on a measured impedance value that exceeds the assigned baseline impedance value by more than a predetermined amount.

In some embodiments, the step of determining a confidence value associated with the baseline impedance value includes incrementally increasing the confidence value of the first electrode based on a measured impedance value that is within a predetermined tolerance range of the assigned baseline impedance value.

In some embodiments, the step of determining a confidence value associated with the baseline impedance value includes decreasing the confidence value if the measured impedance value is outside the predetermined tolerance range of the assigned baseline impedance value.

In some embodiments, the step of determining a confidence value associated with the baseline impedance value further includes incrementally increasing the confidence value based on impedance data collected for a second electrode in the plurality of electrodes, the second electrode paired with the first electrode.

In some embodiments, the step of determining a confidence value associated with the baseline impedance value further includes incrementally increasing the confidence value based on impedance data collected for additional pairs of electrodes in the plurality of electrodes.

According to another aspect, a method of assessing confidence in a baseline impedance value for a first electrode in a plurality of electrodes includes applying drive signals between the first electrode and a second electrode in the plurality of electrodes, the first and second electrodes forming a pair and measuring a bipolar electrode complex impedance (BECI) value for the first electrode generated in response to the drive signals. The method may further include determining a baseline BECI value for the first electrode, the baseline BECI value being a first minimum BECI value measured during a first predetermined time interval that is greater than a predetermined lower threshold and less than a predetermined upper limit and determining tissue contact based on the measured BECI value being greater than the baseline BECI value by a predetermined amount during a second time interval. The method may further include assigning a confidence state for the baseline BECI value based, at least in part, on measured BECI values for the first electrode.

The method of the preceding paragraph can optionally include, additionally and/or alternatively any, one or more of the following features, steps, configurations and/or additional components.

For example, the step of assigning a confidence state for the baseline BECI value may further include increasing the confidence state when a second minimum BECI value is measured during a second predetermined time interval and the second minimum BECI value is greater than the predetermined lower threshold, less than the predetermined upper limit and within a predetermined tolerance range of the first minimum BECI value and decreasing the confidence state and setting a new baseline BECI value when the second minimum BECI value is outside the predetermined tolerance range of the first minimum BECI value.

In some embodiments, decreasing the confidence state and setting a new baseline BECI value utilizing the second minimum BECI value as the new baseline value further includes repeating the steps of determining tissue contact and assigning a confidence state.

In some embodiments, assigning a confidence state for the baseline BECI value is further based on measured BECI values for the second electrode.

In some embodiments, assigning a confidence state for the baseline BECI value further includes increasing the confidence state when the second electrode has a minimum BECI value that is within a predetermined tolerance range of the first or second minimum BECI value of the first electrode.

In some embodiments, assigning a confidence state for the baseline BECI value is further based on measured BECI values for additional pairs of electrodes in the plurality of electrodes.

In some embodiments, assigning a confidence state for the baseline BECI value further includes increasing the confidence state for every additional pair of electrodes that has an average baseline BECI value that is within a predetermined tolerance range of the first or second minimum BECI value of the first electrode.

According to another aspect, a system for use with a medical device having a plurality of electrodes and configured for insertion within a patient includes a signal generator, a measurement circuit, and a contact assessment module. In some embodiments, the signal generator is configured to apply a plurality of drive signals across each electrode in the plurality of electrodes and the measurement circuit is configured to measure responses of the plurality of electrodes to the drive signals and generate an impedance value for each electrode in the plurality of electrodes. In some embodiments, a contact assessment module is configured to determine a baseline impedance value for each electrode and determine a confidence state of the baseline impedance value for each electrode based, at least in part, on measured impedance values for that particular electrode.

The system of the preceding paragraph can optionally include, additionally and/or alternatively any, one or more of the following features, steps, configurations and/or additional components.

For example, the confidence state determined for each electrode may be based on measured impedance values for that particular electrode and measured impedance values for other electrodes in the plurality of electrodes.

In some embodiments, the contact assessment module may utilize the baseline impedance value for an electrode to determine contact status of the electrode when the confidence state is at or above a predetermined threshold value.

According to another aspect, a method of determining a baseline impedance value for a first electrode in a plurality of electrodes located on a medical device for tissue contact detection includes measuring an impedance value of the first electrode generated in response to a drive signal to the first electrode and measuring an impedance value for each of the other electrodes in the plurality of electrodes, the impedance value generated in response to a drive signal to each of the other electrodes. The method may further include assigning a baseline impedance value to the first electrode based on a minimum impedance value measured in a predetermined time interval and determining a confidence value associated with the baseline impedance value based on measured BECI values for the first electrode and measured BECI values for one or more of the other electrodes in the plurality of electrodes. The method may further include utilizing the baseline impedance value in determining contact status of the first electrode when the confidence value is at or above a predetermined threshold value.

The invention claimed is:

1. A method of determining a baseline impedance value for a first electrode in a plurality of electrodes located on a medical device for tissue contact detection, the method comprising:
measuring an impedance value of the first electrode generated in response to a drive signal to the first electrode;
assigning a baseline impedance value to the first electrode based on impedance values measured in a predetermined time interval;
determining a confidence value associated with the baseline impedance value; and
utilizing the baseline impedance value in determining contact status of the first electrode when the confidence value is at or above a predetermined threshold value, wherein determining a confidence value associated with the baseline impedance value includes incrementally increasing the confidence value based on a measured impedance value that exceeds the assigned baseline impedance value by more than a predetermined amount.

2. The method of claim 1, wherein assigning a baseline impedance value to the first electrode includes selecting a minimum impedance value measured in the predetermined time interval.

3. The method of claim 2, wherein the minimum impedance value becomes the assigned baseline impedance value if the minimum impedance value is greater than a predetermined impedance threshold and less than a predetermined impedance limit.

4. The method of claim 1, wherein the impedance value is a bipolar electrode complex impedance (BECI) value resulting from applying the drive signal between the first electrode and a second electrode in the plurality of electrodes.

5. The method of claim 1, wherein determining a confidence value associated with the baseline impedance value includes incrementally increasing the confidence value of the first electrode based on a measured impedance value that is within a predetermined tolerance range of the assigned baseline impedance value.

6. The method of claim 5, wherein determining a confidence value associated with the baseline impedance value includes decreasing the confidence value if the measured impedance value is outside the predetermined tolerance range of the assigned baseline impedance value.

7. The method of claim 5, wherein determining a confidence value associated with the baseline impedance value includes incrementally increasing the confidence value based on impedance data collected for a second electrode in the plurality of electrodes, the second electrode paired with the first electrode.

8. The method of claim 7, wherein determining a confidence value associated with the baseline impedance value includes incrementally increasing the confidence value based on impedance data collected for additional pairs of electrodes in the plurality of electrodes.

9. A method of assessing confidence in a baseline impedance value for a first electrode in a plurality of electrodes, the method comprising:
    applying drive signals between the first electrode and a second electrode in the plurality of electrodes, the first and second electrodes forming a pair;
    measuring a bipolar electrode complex impedance (BECI) value for the first electrode generated in response to the drive signals;
    determining a baseline BECI value for the first electrode, the baseline BECI value being a first minimum BECI value measured during a first predetermined time interval that is greater than a predetermined lower threshold and less than a predetermined upper limit;
    determining tissue contact based on the measured BECI value being greater than the baseline BECI value by a predetermined amount during a second time interval; and
    assigning a confidence state for the baseline BECI value based, at least in part, on measured BECI values for the first electrode, wherein assigning a confidence state comprises:
        increasing the confidence state when a second minimum BECI value is measured during a second predetermined time interval and the second minimum BECI value is greater than the predetermined lower threshold, less than the predetermined upper limit and within a predetermined tolerance range of the first minimum BECI value; and
        decreasing the confidence state and setting a new baseline BECI value when the second minimum BECI value is outside the predetermined tolerance range of the first minimum BECI value.

10. The method of claim 9, wherein decreasing the confidence state and setting a new baseline BECI value includes utilizing the second minimum BECI value as the new baseline value, and the method further comprises repeating the steps of determining tissue contact and assigning a confidence state.

11. The method of claim 9, wherein assigning a confidence state for the baseline BECI value is further based on measured BECI values for the second electrode.

12. The method of claim 11, wherein assigning a confidence state for the baseline BECI value comprises increasing the confidence state when the second electrode has a minimum BECI value that is within a predetermined tolerance range.

13. The method of claim 9, wherein assigning a confidence state for the baseline BECI value is further based on measured BECI values for additional pairs of electrodes in the plurality of electrodes.

14. The method of claim 13, wherein assigning a confidence state for the baseline BECI value comprises increasing the confidence state for every additional pair of electrodes that has an average baseline BECI value that is within a predetermined tolerance range.

* * * * *